United States Patent [19]
De Marinis et al.

[11] 3,943,131
[45] Mar. 9, 1976

[54] TRIFLUOROMETHYLMERCAP-TOACETAMIDOCEPHALOSPORINS

[75] Inventors: Robert M. De Marinis, King of Prussia; John R. E. Hoover, Glenside, both of Pa.

[73] Assignee: SmithKline Corporation, Philadelphia, Pa.

[22] Filed: Apr. 22, 1974

[21] Appl. No.: 463,085

Related U.S. Application Data

[62] Division of Ser. No. 273,571, July 20, 1972, Pat. No. 3,828,037.

[52] U.S. Cl. .............................................. 424/246
[51] Int. Cl.² ......................................... A61K 31/54

[58] Field of Search .................................... 424/246

[56] References Cited
UNITED STATES PATENTS
3,647,788   3/1972   Clark et al. ...................... 260/243 C

*Primary Examiner*—Jerome D. Goldberg
*Attorney, Agent, or Firm*—Stuart R. Suter; Alan D. Lourie; William H. Edgerton

[57] ABSTRACT

This invention is directed to antibacterial compounds, in particular, to 7-trifluoromethylmercaptoacetamidocephalosporins.

7 Claims, No Drawings

TRIFLUOROMETHYLMERCAP-
TOACETAMIDOCEPHALOSPORINS

This is a division of application Ser. No. 273,571 filed July 20, 1972, now U.S. Pat. No. 3,828,037.

This invention relates to cephalosporins with a new 7-acyl group, in particular to the 7-trifluoromethylmercaptoacetamidocephalosporins. The compounds have antibacterial activity.

Cephalosporins with a variety of acyl groups at the 7-position have been disclosed and claimed in the prior art. For example, 7-alkylmercaptoacetamidocephalosporanic acids have been disclosed in U.S. Pat. No. 3,297,692 and others. Also, 7-methylmercaptoacetamido-3-[N-n-butyl-N-(2'-diethylaminoethyl)aminothiocarbonylthiomethyl]-3-cephem-4-carboxylic acid and other similar compounds have been disclosed and/or claimed in U.S. Pat. Nos. 3,239,515, 3,239,516 and 3,573,298. However, no cephalosporins with a trifluoromethylmercapto group in the 7-acyl substituent have been described.

The novel compounds of this invention have the following structure:

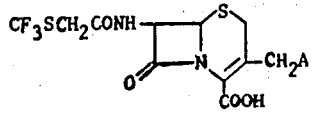

in which:

A is hydrogen, acetoxy, pyridinium, methoxy, methylthio or S-Het;

Het is a 5 or 6 membered heterocyclic ring containing 1–4 hetero atoms selected from the group consisting of N. O and S and being unsubstituted or substituted with one or two groups selected from the group consisting of alkyl, alkoxy, alkylthio, each alkyl residue being one to four carbon atoms; $C_3$–$C_4$ cycloalkyl, halogen, hydroxy, mercapto, trifluoromethyl and $NR_2$; and R is hydrogen or $C_1$–$C_6$ alkyl.

A preferred group of compounds is that where A is S-Het. Particularly preferred are those compounds where Het is a substituted or unsubstituted tetrazole, thiadiazole, oxadiazole or triazole.

Included within the scope of this invention are the pharmaceutically acceptable salts that are formed by reaction of the cephalosporin acid with a pharmaceutically acceptable base. It is recognized that when the substituent on the heterocyclic group is hydroxy or mercapto that it is possible for the substituent to exist in more than one tautomeric form, i.e. the hydroxy or oxo and the mercapto or thiono forms. The compounds may exist exclusively as one tautomer or may be in equilibrium between the other forms; however, these are all included within the scope of this invention.

The compounds are prepared by acylation of the appropriate 7-aminocephalosporin, for example, 7-aminocephalosporanic acid (7-ACA), 7-aminodesacetoxycephalosporanic acid (7-ADCA) or 7-amino-3-heterocyclothiomethyl-3-cephem-4-carboxylic acid, with trifluoromethylmercaptoacetic acid. The carboxyl group of the acetic acid is activated by one of the common methods known to one skilled in the art such as mixed anhydride, acid halide or activated ester. In addition, acylation of esters of the cephalosporin nucleus may be done by using a coupling reagent such as dicyclohexylcarbodiimide (DCC) or N,N'-carbonyldiimidazole.

Trifluoromethylmercaptoacetic acid is prepared by treating iodoacetic acid with silver trifluoromethylmercaptan. The acetic acid is converted to an activated ester by condensing N-hydroxysuccinimide and the acid, with DCC being used as the condensing reagent. This activated ester is then used to acylate the appropriate 7-aminocephalosporin. Alternatively, trifluoromethylmercaptoacetyl chloride, prepared from trifluoromethylsulfenyl chloride and ketene [J. Org. Chem. 37:1340(1972)], may be used as the acylating reagent.

The compounds of this invention have antibacterial activity against both Gram-positive and Gram-negative organisms. Minimum inhibitory concentrations (MIC) ranged from 0.1 to >200 μg./ml. in an in vitro screen against a broad variety of bacteria; however, most of the MIC's were less than 50 μg./ml. The MIC's for 7-trifluoromethylmercaptoacetamidocephalosporanic acid (I), 7-trifluoromethylmercaptoacetamido-3-(1-methyltetrazol-5-ylthiomethyl)-3-cephem-4-carboxylic acid (II), and 7-trifluoromethylmercaptoacetamido-3-(5-methyl-1,3,4-thiadiazol-2-ylthiomethyl)-3-cephem-4-carboxylic acid (III) against representative bacteria are shown in Table I. In addition, the compounds exhibit antibacterial activity in an in vivo screen screen when administered subcutaneously.

TABLE I

| Bacteria | MIC (μg./ml.) | | |
|---|---|---|---|
| | I | II | III |
| S. aureus HH 127 | 0.4 | 0.4 | 0.4 |
| Strep. pyog. C 203 | 0.1 | 0.1 | 0.1 |
| Strep. faecalis HH 34358 | 25 | 25 | 12.5 |
| E. coli. HH 33779 | 6.3 | 1.6 | 3.1 |
| K. pneumo. SK 4200 | 0.8 | 0.8 | 1.6 |
| Pseudomonas sp. HH 63 | <200 | <200 | <200 |
| Entero. aerogenes | 50 | 1.6 | 6.3 |

These compounds are formulated and administered in the same manner as other cephalosporin compounds. The dose and mode of administration are within the skill of the art.

The following examples illustrate the invention but are not to be understood as limiting the scope thereof.

EXAMPLE 1

N-Hydroxysuccinimidyl trifluoromethylmercaptoacetate

Trifluoromethylmercaptoacetic acid was prepared by allowing equal molar quantities of trifluoromethyl mercaptan silver salt and iodoacetic acid to stand at room temperature in acetone for 11 days. The solid was collected and washed with acetone. The combined filtrates and washings were decolorized with charcoal and evaporated to an oil which was distilled; b.p. 90°–100°λ /2–3 mm.

A solution of the above acetic acid (4.8 g., 0.03 mol.) and N-hydroxysuccinimide (3.45 g., 0.03 mol.) in tetrahydrofuran (50 ml.) was stirred and cooled to 0° before dicyclohexylcarbodiimide (6.2 g., 0.031 mol.) was added in one portion. The reaction was stirred at 0° for one hour and then overnight at room temperature. The precipitate was filtered and washed with THF. Evaporation of the filtrate gave an oil which crystallized on standing. The solid was taken up in ether, boiled with charcoal and filtered to give a solution which gave a yellow solid on evaporation. Recrystallization from carbon tetrachloride gave the pure product; m.p. 130°.

By similar methods the trifluoromethylmercaptoacetic acid can be reacted with other hydroxy compounds to give other activated esters such as 2,4-dinitrophenyl.

EXAMPLE 2

7-Trifluoromethylmercaptoacetamidocephalosporanic acid

7-Aminocephalosporanic acid (544 mg., 2 mmol.) was suspended in dry DMF (10 ml.) and triethylamine was added until solution was effected. The activated ester from Example 1 (514 mg., 2 mmol.) was added and the reaction was stirred for 2.5 hours at room temperature. The mixture was poured into water (50 ml.) and the aqueous solution was acidified and then extracted with ethyl acetate. The dried extracts were evaporated to an oil which crystallized. The solid product was collected, triturated with ether, and dried, m.p. 139°(dec.).

EXAMPLE 3

7-trifluoromethylmercaptoacetamido-3-methyl-3-cephem-4-carboxylic acid

7-Aminodesacetoxycephalosporanic acid (1.07 g., 5 mmol.) was suspended in dry DMF (25 ml.) and 1,5-diazobicyclo-[4.3.0]non-5-ene was added until a slight cloudiness just remained. The activated ester from Example 1 (1.28 g., 5 mmol.) was added and the mixture was stirred for two hours at room temperature. The reaction was poured into water (200 ml.), acidified, and extracted with ethyl acetate. The extracts were washed with water, dried and evaporated to a product which crystallized on standing. The product was recrystallized from chloroform; m.p. 108°(dec.).

EXAMPLE 4

7-Trifluoromethylmercaptoacetamido-3-(5-methyl-1,3,4-thiadiazol-2-ylthiomethyl)-3-cephem-4-carboxylic acid To a suspension of 7-amino-3-(5-methyl-1,3,4-thiadiazol-2-ylthiomethyl)-3-cephem-4-carboxylic acid (628 mg., 2 mmol.) in dry DMF (20 ml.) was added triethylamine until only a slight cloudiness remained. The activated ester of Example 1 (514 mg., 2 mmol.) was added in one portion and the reaction mixture was stirred for three hours at room temperature. The reaction was poured into ice water (100 ml.) and the aqueous solution was acidified to pH 1.5 with 3N HCl and extracted with ethyl acetate. The combined extracts were washed with water and then saturated saline solution. The dried organic phase, containing the title compound, was concentrated to ca. 20 ml. The dropwise addition of a 30% solution of sodium 2-ethylhexanoate in isopropanol precipitated the sodium salt which was collected and dried.

EXAMPLE 5

7-Trifluoromethylmercaptoacetamido-3-(1-methyl-tetrazol-5-ylthiomethyl)-3-cephem-4-carboxylic acid 7-Amino-3-(1-methyl-tetrazol-5-ylthiomethyl)-3-cephem-4-carboxylic acid (984 mg., 3 mmol.) and the activated ester from Example 1 (771 mg., 3 mmol.) were reacted by the same procedure as in Example 4. Evaporation of the washed and dried extracts gave the title compound. The product was dissolved in ethyl acetate, heated with charcoal for 15 minutes, filtered, and treated with a 30% solution of sodium 2-ethylhexanoate in isopropanol. The sodium salt was precipitated by the addition of ether, collected and dried. The dried powder was dissolved in acetonitrile at room temperature and allowed to stand. It deposited white crystals of the sodium salt of the title compound.

EXAMPLE 6

7-Trifluoromethylmercaptoacetamido-3-(5-methyl-1,2,4-triazol-3-ylthiomethyl)-3-cephem-4-carboxylic acid 7-Amino-3-(5-methyl-1,2,4-triazol-3-ylthiomethyl)-3-cephem-4-carboxylic acid (1.14 g., 3.5 mmol.) and the activated ester of Example 1 (0.89 g., 3.5 mmol.) were reacted according to the procedure of Example 4. Evaporation of the ethyl acetate extracts gave a gummy residue which crystallized on standing. The product was recrystallized from acetonitrile to give the pure title compound.

EXAMPLE 7

7-Trifluoromethylmercaptoacetamido-3-(5-hydroxy-1,2,4-triazol-3-ylthiomethyl)-3-cephem-4-carboxylic acid To a cold solution (−20°) of 7-amino-3-(5-hydroxy-1,2,4-triazol-3-ylthiomethyl)-3-cephem-4-carboxylic acid (3.39 g., 0.01 mole) in a mixture of acetone (62.5 ml.) and 3% $NaHCO_3$ (62.5 ml.) is added dropwise over a 30 minute period a solution of trifluoromethylmercaptoacetyl chloride (2.24 g., 0.012 mol.) in acetone (20 ml.) The solution is maintained at pH 8 by adding 10% sodium hydroxide as needed. The reaction is stirred for 20 minutes at −15° to −20° and then allowed to warm to room temperature. The solution is washed with ether, covered with ethyl acetate and acidified to pH 2. The aqueous phase is separated and extracted with ethyl acetate. The combined ethyl acetate phases are combined, washed with water, dried, and evaporated to give the title compound.

EXAMPLE 8

When an equivalent amount of a 7-amino-3-heterocycliothiomethyl-3-cephem-4-carboxylic acid listed below is substituted in the procedure of Example 4 for 7-amino-3-(5-methyl-1,3,4-thiadiazol-2-ylthiomethyl)-3-cephem-4-carboxylic acid, the apropriate 7-trifluoromethylmercaptoacetamido-3-heterocycliothiomethyl-3-cephem-4-carboxylic acid is obtained.

7-Amino-3-(1,3,4-thiadiazol-2-ylthiomethyl)-3-cephem-4-carboxylic acid.

7-Amino-3-(5-trifluoromethyl-1,3,4-thiadiazol-2-ylthiomethyl)-3-cephem-4-carboxylic acid.

7-Amino-3-(5-ethyl-1,3,4-thiadiazol-2-ylthiomethyl)-3-cephem-4-carboxylic acid.

7-Amino-3-(5-n-butyl-1,3,4-thiadiazol-2-ylthiomethyl)-3-cephem-4-carboxylic acid.

7-Amino-3-(5-dimethylamino-1,3,4-thiadiazol-2-ylthiomethyl)-3-cephem-4-carboxylic acid.

7-Amino-3-(5-mercapto-1,3,4-thiadiazol-2-ylthiomethyl)-3-cephem-4-carboxylic acid.

7-Amino-3-(3-methylthio-1,2,4-thiadiazol-5-ylthiomethyl)-3-cephem-4-carboxylic acid.

7-Amino-3-(3-methyl-1,2,4-thiadiazol-5-ylthiomethyl)-3-cephem-4-carboxylic acid.

7-Amino-3-(tetrazol-5-ylthiomethyl)-3-cephem-4-carboxylic acid.

7-Amino-3-(1,2,4-triazol-3-ylthiomethyl)-3-cephem-4-carboxylic acid.

7-Amino-3-(4-methyl-1,2,4-triazol-3-ylthiomethyl)-3-cephem-4-carboxylic acid.

7-Amino-3-(4,5-dimethyl-1,2,4-triazol-3-ylthiomethyl)-3-cephem-4-carboxylic acid.

7-Amino-3-(1,3-dimethyl-1,2,4-triazol-5-ylthiomethyl)-3-cephem-4-carboxylic acid.

7-Amino-3-(4-methyl-5-trifluoromethyl-1,2,4-triazol-3-ylthiomethyl)-3-cephem-4-carboxylic acid.

7-Amino-3-(5-ethyl-1,2,4-triazol-3-ylthiomethyl)-3-cephem-4-carboxylic acid.

7-Amino-3-(4-ethyl-1,2,4-triazol-3-ylthiomethyl)-3-cephem-4-carboxylic acid.

7-Amino-3-(1-methyl-1,2,4-triazol-5-ylthiomethyl)-3-cephem-4-carboxylic acid.

7-Amino-3-(1-methyl-1,2,4-triazol-3-ylthiomethyl)-3-cephem-4-carboxylic acid.

7-Amino-3-(1-ethyl-1,2,4-triazol-5-ylthiomethyl)-3-cephem-4-carboxylic acid.

7-Amino-3-(1-ethyl-1,2,4-triazol-3-ylthiomethyl)-3-cephem-4-carboxylic acid.

7-Amino-3-(4-allyl-1,2,4-triazol-3-ylthiomethyl)-3-cephem-4-carboxylic acid.

7-Amino-3-(5-methoxymethyl-1,2,4-triazol-3-ylthiomethyl)-3-cephem-4-carboxylic acid.

7-Amino-3-(5-cyclopropyl-1,2,4-triazol-3-ylthiomethyl)-3-cephem-4-carboxylic acid.

7-Amino-3-(5-bromo-1,2,4-triazol-3-ylthiomethyl)-3-cephem-4-carboxylic acid.

7-Amino-3-(5-hydroxy-4-methyl-1,2,4-triazol-3-ylthiomethyl)-3-cephem-4-carboxylic acid.

7-Amino-3-(5-hydroxy-4-ethyl-1,2,4-triazol-3-ylthiomethyl)-3-cephem-4-carboxylic acid.

7-Amino-3(1,2,3-triazol-4-ylthiomethyl)-3-cephem-4-carboxylic acid.

7-Amino-3(1-methyl-1,2,3-triazol-5-ylthiomethyl)-3-cephem-4-carboxylic acid.

7-Amino-3-(1,3,4-oxadiazol-2-ylthiomethyl)-3-cephem-4-carboxylic acid.

7-Amino-3-(5-methyl-1,3,4-oxadiazol-2ylthiomethyl)-3-cephem-4-carboxylic acid.

7-Amino-3-(4-pyrimidylthiomethyl)-3-cephem-4-carboxylic acid.

7-Amino-3-(2-pyrazinylthiomethyl)-3-cephem-4-carboxylic acid.

7-Amino-3-(3-pyridylthiomethyl)-3-cephem-4carboxylic acid.

7-Amino-3-(4-pyridylthiomethyl)-3-cephem-4-carboxylic acid.

EXAMPLE 9

When an equivalent amount of 7-amino-3-methoxymethyl-3-cephem-4-carboxylic acid is substituted into the procedure of Example 4, 7-trifluoromethylmercaptoacetamido-3-methoxymethyl-3-cephem-4-carboxylic acid is obtained.

Acylation of 7-amino-3-methylthiomethyl-3-cephem-4-carboxylic acid according to the procedure of Example 4 gives 7-trifluoromethylmercaptoacetamido-3-methylthiomethyl-3-cephem-4-carboxylic acid.

EXAMPLE 10

7-Trifluoromethylmercaptoacetamido-3-(1-pyridiniummethyl)-3-cephem-4-carboxylic acid To a solution of 7-trifluoromethylmercaptoacetamidocephalosporanic acid sodium salt (4.36 g., 0.01 mol.) in water (25 ml.) is added potassium thiocyanate (2.23 g., 0.023 mol.) and pyridine (2.2 ml. 0.028 mol.). The reaction is heated at 65°–70° for seven hours and then is cooled. The mixture is diluted with water (100 ml.) and the aqueous solution is chromatographed on a column of cross-linked polystyrene polymer (Amberlite XAD-2). The inorganic salts are eluted with water and then the product is eluted with 95% ethanol. Evaporation of the eluant gives the product.

EXAMPLE 11

An injectable pharmaceutical composition is prepared by dissolving 500 mg. of sodium 7-trifluoromethylmercaptoacetamido-3-(1-methyltetrazol-5-ylthiomethyl)-3-cephem-4-carboxylate in sterile water or sterile normal saline solution (1–2 ml.). Other cephalosporins of this invention are formulated in a similar manner.

An antibacterial capsule is comprised of the following components:

| | |
|---|---|
| cephalosporin | 500 mg. |
| lactose | 250 mg. |
| magnesium stearate | 75 mg. |

We claim:

1. A pharmaceutical composition comprising an antibacterially effective amount of the compound of the formula

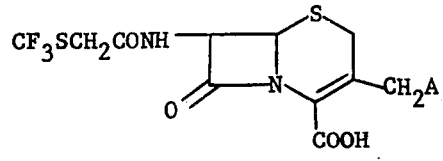

in which:
A is S-Het;
Het is a 5 or 6 membered heterocyclic ring containing 1–4 hetero atoms selected from the group consisting of N, O and S and being unsubstituted or substituted with one or two groups selected from the group consisting of alkyl, alkoxy, alkylthio, each alkyl residue being one to four carbon atoms; $C_3$–$C_4$ cycloalkyl, halogen, hydroxy, mercapto, trifluoromethyl and $NR_2$; and
R is hydrogen or $C_1$14 $C_6$ alkyl, or a pharmaceutically acceptable salt thereof and sterile water or sterile saline as carrier therefor.

2. A pharmaceutical composition as claimed in claim 1 comprising an antibacterially effective amount of a compound where Het is tetrazolyl, thiadiazolyl, triazolyl, or oxadiazolyl, unsubstituted or substituted with one or two $C_1$–$C_4$ alkyl groups, a hydroxy or a mercapto group and sterile water or sterile saline as carrier therefor.

3. A pharmaceutical composition as claimed in claim 2 comprising an antibacterially effective amount of the compound 7-trifluoromethylmercaptoacetamido-3-(5-methyl-1,3,4-thiadiazol-2-ylthiomethyl)-3-cephem-4- carboxylic acid and sterile water or sterile saline as carrier therefor.

4. A pharmaceutical composition as claimed in claim 2 comprising an antibacterially effective amount of the compound 7-trifluoromethylmercaptoacetamido-3-(1-methyltetrazol-5-ylthiomethyl)-3-cephem-4-carboxylic acid and sterile water or sterile saline as carrier therefor.

5. A pharmaceutical composition as claimed in claim 2 comprising an antibacterially effective amount of the compound 7-trifluoromethylmercaptoacetamido-3-(1,2,3-triazol-4-ylthiomethyl)-3-cephem-4-carboxylic acid and sterile water or sterile saline as carrier therefor.

6. A pharmaceutical composition as claimed in claim 2 comprising an antibacterially effective amount of the compound 7-trifluoromethylmercaptoacetamido-3-(5-methyl-1,2,4-triazol-3-ylthiomethyl)-3-cephem-4-carboxylic acid and sterile water or sterile saline as carrier therefor.

7. A pharmaceutical composition as claimed in claim 2 comprising an antibacterially effective amount of the compound 7-trifluoromethylmercaptoacetamido-3-(5-hydroxy-1,2,4-triazol-3-ylthiomethyl)-3-cephem-4-carboxylic acid and sterile water or sterile saline as carrier therefor.

* * * * *

UNITED STATES PATENT AND TRADEMARK OFFICE
CERTIFICATE OF CORRECTION

PATENT NO. : 3,943,131
DATED : March 9, 1976
INVENTOR(S) : Robert M. DeMarinis and John R. E. Hoover It is certified that error appears in the above-identified patent and that said Letters Patent are hereby corrected as shown below:

Column 6, line 55: "$C_1 14C_6$" should read -- $C_1-C_6$ --

Signed and Sealed this

Twenty-seventh Day of July 1976

[SEAL]

Attest:

RUTH C. MASON
*Attesting Officer*

C. MARSHALL DANN
*Commissioner of Patents and Trademarks*